United States Patent [19]
Benatti et al.

[11] Patent Number: 5,817,496
[45] Date of Patent: Oct. 6, 1998

[54] RECOMBINANT KAT ENZYME FROM RAT

[75] Inventors: Luca Benatti; Jerome Breton; Carmela Speciale, all of Milan, Italy; Etsuo Okuno, Wakayama, Japan; Robert Schwarcz, Baltimore, Md.; Monica Mosca, Milan, Italy

[73] Assignees: Pharmacia & UpJohn S.P.A., Milan, Italy; University of Maryland at Baltimore, Baltimore, Md.

[21] Appl. No.: 271,667

[22] Filed: Jul. 7, 1994

[51] Int. Cl.[6] .................................................. C12N 9/10
[52] U.S. Cl. ............................. 435/193; 536/23.2
[58] Field of Search ................... 435/232, 193; 536/23.2

[56] References Cited

PUBLICATIONS

Mosca et al, "Molecular Cloning of Rat Kynurenine Aminotransferase: Identity With Glutamine Transaminase K", *FEBS Letter*, 353:21–24 (1994).

Baran et al., *J. Neurochem.* vol. 62, pp. 730–738, 1994.

Asada et al., *J. Biochem.*, 99:1101–1110, 1986.

Mawal et al., *J. Biochem.* 279:595–599, 1991.

Takeuchi et al., *Biochem. Biophys. Acta*, 743:323–330, 1983.

*Primary Examiner*—Keith D. Hendricks
*Attorney, Agent, or Firm*—Sughrue, Mion, Zinn, Macpeak & Seas

[57] ABSTRACT

Disclosed are isolated DNAs encoding a kynurenine aminotransferase selected from the group consisting of: (a) an isolated DNA sequence which encodes rat KAT; (b) an isolated DNA sequence which hybridizes to the isolated DNA sequence of (a) above and which encodes a KAT enzyme; and (c) an isolated DNA sequence differing from the isolated DNA sequences of (a) and (b) above in codon sequence due to the degeneracy of the genetic code, and which encodes a KAT enzyme. Also disclosed are vectors and host cells containing the same; oligonucleotide probes for identifying kynurenine aminotransferase; and isolated and purified kynurenine aminotransferase.

1 Claim, 1 Drawing Sheet

RECOMBINANT KAT ENZYME FROM RAT

BACKGROUND OF THE INVENTION

The present invention relates to DNA sequences encoding for rat kynurenine aminotransferase.

The enzyme kynurenine aminotransferase (known in the art as KAT) catalyzes the biosynthesis of kynurenic acid (KYNA) from kynurenine (KYN) and is singularly responsible for the regulation of extracellular KYNA concentrations in the brain (J. Neurochem., 57, 533–540, 1991).

KYNA is an effective excitatory amino acid (EAA) receptor antagonist with a particularly high affinity to the glycine modulatory site of the N-methyl-D-aspartate (NMDA) receptor complex (J. Neurochem., 52, 1319–1328, 1989). As a naturally occurring brain metabolite (J. Neurochem., 51, 177–180, 1988 and Brain Res., 454, 164–169, 1988), KYNA probably serves as a negative endogenous modulator of cerebral glutamatergic function (Ann. N.Y. Acad. Sci., vol. 648, p. 140–153, 1992).

EAA receptors and in particular NMDA receptors are known to play a central role in the function of the mammalian brain (J. C. Watkins and G. L. Collingridge —eds.—, In: The NMDA receptor, Oxford University press, Oxford, p. 242, 1989). For example, NMDA receptor activation is essential for cognitive processes, such as, for example, learning and memory (J. C. Watkins and G. L. Collingridge —eds.—, In: The NMDA receptor, Oxford University press, Oxford, p. 137–151, 1989) and for brain development (Trends Pharmacol. Sci., 11, 290–296, 1990).

It follows that a reduction in NMDA receptor function will have detrimental consequences for brain physiology and, consequently, for the entire organism. For example, the decline in the number of NMDA receptors which occurs in the aged brain (Synapse, 6, 343–388, 1990) is likely associated with age-related disorders of cognitive functions.

In the brain, KYNA concentrations and the activity of KYNA's biosynthetic enzyme KAT show a remarkable increase with age (Brain Res. 558, 1–5, 1992 and Neurosci. Lett., 94, 145–150, 1988). KAT inhibitors, by providing an increase of the glutamatergic tone at the NMDA receptor, could therefore be particularly useful in situations where NMDA receptor function is insufficient and/or KAT activity and KYNA levels are abnormally enhanced. Hence they could be particularly useful in the treatment of the pathological consequences associated with the aging processes in the brain which are, for example, cognitive disorders including, e.g., attentional and memory deficits and vigilance impairments in the elderly.

KAT inhibitors may also be useful in the treatment of perinatal brain disorders which may be related to irregularities in the characteristic region specific pattern of postnatal KAT development (H. Baran and R. Schwarcz: Regional differences in the ontogenic pattern of KAT in the brain, Dev. Brain Res., 74, 283–286, 1993).

In subcellular fractionation studies KAT activity was recovered either in the cytosol and in mitochondria (J. Neurochem., 57, 533–540, 1991).

Most nuclear-encoded precursors of mitochondrial proteins contain amino-terminal presequences (Pfanner and Neupert, In: Current Topics in Bioenergetics, Vol. 15, Lee ed., New York Academic Press, p. 177–219, 1987 and Nicholson and Neupert, In: Protein Transfer and Organelle Biogenesis, R. C. Das and P. W. Robins, eds. New York Academic Press, 1988). These presequences are required for the precursor to enter the mitochondrial matrix, where they are proteolytically removed (Hurt et al., FEBS Lett. 178, 306, 1984, Horwich et al., EMBO J. 4, 1129, 1985). This cleavage is not essential for completing import but is necessary for further assembly of the newly imported polypeptides into functional complexes (Zwizinski and Neupert, J. Biol. Chem., 258, 13340, 1983; Lewin and Norman, J. Biol. Chem., 258, 6750, 1983; Ou et al. J. Biochem., 100, 1287, 1986). Precursor targeting sequences differ considerably in their structures. One of the few common themes is the high content of positively charged amino acids and of hydroxylated amino acids. Presequences may form an amphipathic structure in the form of either $\alpha$-helices or $\beta$-sheets (von Heijne, EMBO J., 5, 1335, 1986; Roise et al., EMBO J., 5, 1327, 1986; Vassarotti et al., EMBO J., 6, 705, 1987). Despite the large variability of the sequences of mitochondrial leader peptides, relatively minor alterations of the presequence can prevent cleavage by the processing peptidase (Hurt et al., J. Biol. Chem. 262, 1420, 1987). This suggests that distinct, but up to now undefined, structural elements are required for cleavage. Similarly, the cleavage sites show wide variation among different precursors of a single organism and among precursors of different organisms.

Interestingly, using the protein algoritm described by Gavel and von Heijne (Protein Engineering, 4, 33–37, 1990), a potential mitochondrial transit peptide is predicted in position 1 to 24 of the deduced protein of only cDNA-2 disclosed in the present invention (see FIG. 3 and Example 3).

Recently Perry et al. (Mol. Pharm., 43:660–665, 1993) reported the cloning of a cDNA coding for rat kidney cytosolic cysteine conjugate $\beta$-lyase. When the cDNA was inserted into the expression vector pVS1000 and transfected into COS-1 tissue culture cells, a 7–10 fold increase in cytosolic $\beta$-lyase and glutamine transaminase K activities were detected.

The deduced amino acid sequence of rat $\beta$-lyase is identical to the deduced amino acid sequence of cDNA-1 (rat KAT) except for two residues (see SEQ ID NO:5). Moreover the existence of cDNA-2 was not reported by Perry et al. (Mol. Pharm., 43:660–665, 1993).

Whereas the identity with cysteine conjugate $\beta$-lyase and glutamine transaminase K is well documented (Abraham, D. G. and Cooper, A. J. L.; Analytical Biochem., 197:421–427, 1991), there are no reports indicating identity of kynurenine transaminase K neither with $\beta$-lyase nor with glutamine transaminase K.

SUMMARY OF THE INVENTION

We now report the cloning of rat kynurenine aminotransferases.

A first aspect of the present invention are isolated DNA sequences encoding KAT enzyme selected from the group consisting of:(a) isolated DNA sequence which encodes rat KAT; (b) isolated DNA sequence which hybridizes to isolated DNA sequence of (a) above and which encodes a KAT enzyme; and (c) isolated DNA sequence differing from the isolated DNA sequences of (a) and (b) above in codon sequence due to the degeneracy of the genetic code, and which encodes a KAT enzyme.

A second aspect of the present invention are vectors comprising a cloned DNA sequence as given above.

A third aspect of the present invention are host cells transformed with a vector as given above.

A fourth aspect of the present invention is an oligonucleotide probe capable of selectively hybridizing to a DNA comprising a portion of a gene coding for a KAT enzyme.

A fifth aspect of the present invention is isolated and purified KAT enzyme which is coded for by a DNA sequence selected from the group consisting of:(a) isolated DNA sequence which encodes rat KAT; (b) isolated DNA sequence which hybridizes to isolated DNA sequence of (a) above and which encodes a KAT enzyme; and (c) isolated DNA sequence differing from the isolated DNA sequences of (a) and (b) above in codon sequence due to the degeneracy of the genetic code, and which encodes a KAT enzyme.

BRIEF DESCRIPTION OF THE DRAWINGS

FIG. 1 cytosolic enzyme activities in transfected COS-1 cells: A, glutamine transaminase K activity; B, kynurenine transaminase activity. Sense: PSVL-KAT transfected COS-1 cells where cDNA-1 is in the sense orientation. Antisense: pSVL-KAT transfected COS-1 cells where cDNA-1 is in reverse orientation. Each value is the mean of three separate experiments.

DETAILED DESCRIPTION OF THE INVENTION

Figure 1A:
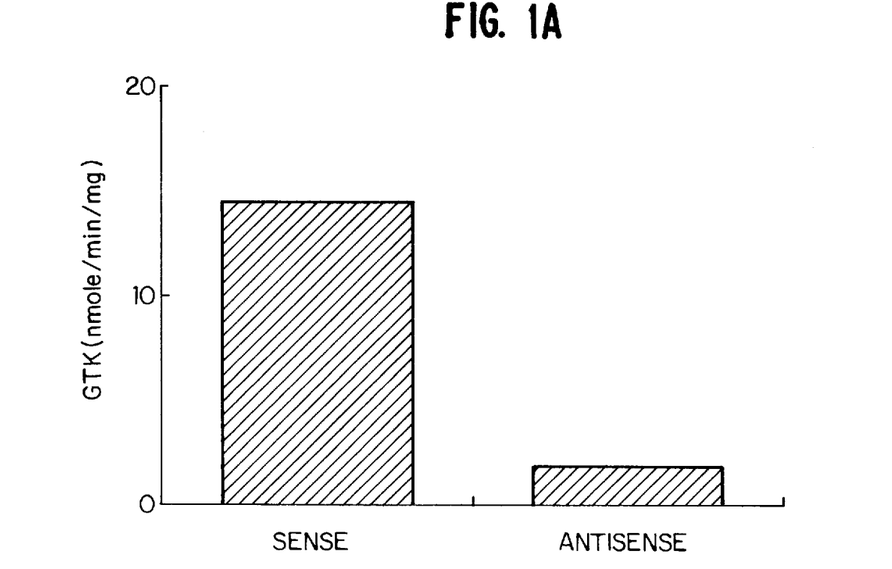
Figure 1B:
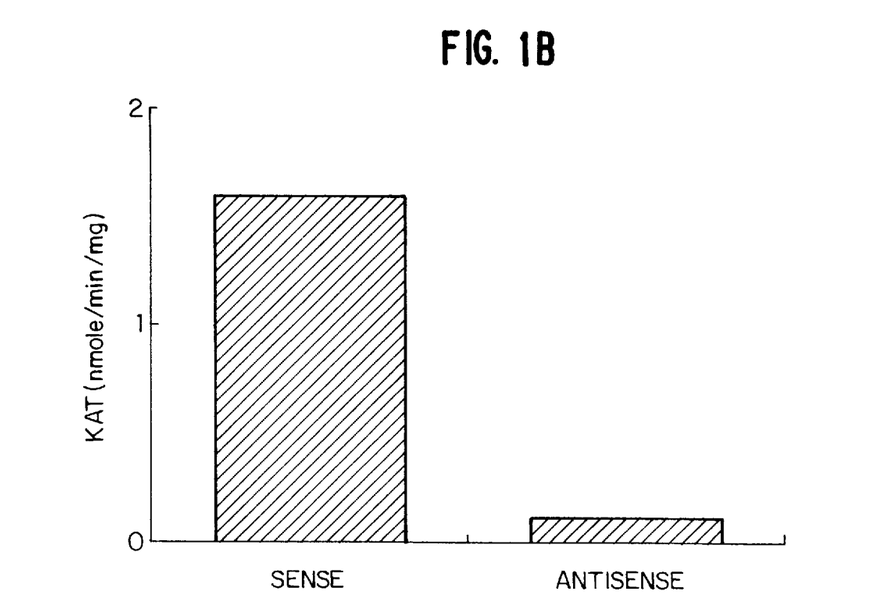

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code.

The rat kynurenine aminotransferase enzyme of the present invention includes proteins homologous to, and having essentially the same biological properties as, the protein coded for by the nucleotide sequences herein disclosed. This definition is intended to encompass natural allelic variants of KAT sequence.

Cloned genes of the present invention may code for KAT of any species of origin, but preferably code for enzymes of mammalian origin. Thus, DNA sequences which hybridize to the sequences given in (SEQ ID NO:5) and (SEQ ID NO:6) and which code for expression of KAT are also an aspect of this invention. Conditions which will permit other DNA sequences which code for expression of KAT to hybridize to the sequences given in (SEQ ID NO:5) and (SEQ ID NO:6) can be determined in a routine manner. Further, DNA sequences which code for polypeptides coded for by the sequences given in (SEQ ID NO:5) and (SEQ ID NO:6) or sequences which hybridize thereto and code for a KAT enzyme, but which differ in codon sequence from these due to degenerancy of the genetic code, are also an aspect of this invention. The degenerancy of the genetic code, which allows different nucleic acid sequences to code for the same protein or peptide, is well known in the literature. See e.g. U.S. Pat. No. 4,757,006 to Toole et al. at Col. 2, Table 1.

DNA which encodes the KAT enzyme may be obtained by a variety of means well known to the expert in the art and disclosed by, for example, Maniatis et al., Molecular cloning: a laboratory manual, Second Edition, Cold Spring Harbor Press, Cold Spring Harbor, N.Y. (1989). For example, DNA which encodes the KAT enzyme may be obtained by screening of mRNA or genomic DNA with oligonucleotide probes generated from the KAT enzyme gene sequence information provided herein. Probes may be labeled with a detectable group such as a fluorescent group, a radioactive atom or a chemiluminescent group in accordance with known procedures and used in conventional hybridization assays, as described by, for example, Maniatis et al., Molecular cloning: a laboratory manual, Second Edition, Cold Spring Harbor Press, Cold Spring Harbor, N.Y. (1989).

KAT gene sequences may alternatively be recovered by use of the polymerase chain reaction (PCR) procedure, with the PCR oligonucleotide primers described herein or with oligonucleotide primers being produced from the KAT enzyme sequences provided herein. See U.S. Pat. Nos. 4,683,195 to Mullis et al. and U.S. Pat. No. 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

The recombinant DNA molecules of the present invention can be produced through any of a variety of means well known to the expert in the art and disclosed by, for example, Maniatis et al., Molecular cloning: a laboratory manual, Second Edition, Cold Spring Harbor Press, Cold Spring Harbor, N.Y. (1989). In order to replicate the KAT enzyme DNA sequences, these must be cloned in an appropriate vector. A vector is a replicable DNA construct. Vectors are used herein either to amplify DNA encoding the KAT enzyme and/or to express DNA which encodes the KAT enzyme. An expression vector is a replicable DNA construct in which a DNA sequence encoding the KAT enzyme is operably linked to suitable control sequences capable of effecting the expression of the KAT enzyme in a suitable host. DNA regions are operably linked when they are functionally related to each other. For example: a promoter is operably linked to a coding sequence if it controls the transcription of the sequence. Amplification vectors do not require expression control domains. All that is needed is the ability to replicate in a host, usually conferred by an origin of replication, and a selection gene to facilitate recognition of transformants.

DNA sequences encoding KAT enzyme may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesiderable joining, and ligation with appropriate ligases. Techniques for such manipulation are disclosed by Maniatis et al., Molecular cloning: a laboratory manual, Second Edition, Cold Spring Harbor Press, Cold Spring Harbor, N.Y. (1989) and are well known in the art.

Expression of the cloned sequence occurs when the expression vector is introduced into an appropriate host cell. If a prokaryotic expression vector is employed, then the appropriate host cell would be any prokaryotic cell capable of expressing the cloned sequences, for example *E. coli*. Similarly, if an eukaryotic expression vector is employed, then the appropriate host cell would be any eukaryotic cell capable of expressing the cloned sequence. A yeast host may be employed, for example *S. cerevisiae*. Alternatively, insect cells may be used, in which case a baculovirus vector system may be appropriate. Another alternative host is a mammalian cell line, for example cos-1 cells.

The need for control sequences into the expression vector will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Vectors useful for practicing the present invention include plasmids, viruses (including phages), retroviruses, and integrable DNA fragments (i.e. fragments integrable into the host genome by homologous recombinantion). The vectors replicate and function independently of the host genome, or may, in some instances, integrate into the genome itself. Expression vectors should contain a promoter which is recognized by the host organism. The promoter sequences of the present invention may be either prokaryotic, eukaryotic or viral. Example of suitable prokaryotic sequences include the $P_R$ and $P_L$ promoters of bacteriophage lambda (The Bacteriophage Lambda, Hershey, A. D., Ed., Cold Spring Harbor Press, Cold Spring Harbor, N.Y. (1973); Lambda II, Hendrix, R. W., Ed., Cold Spring Harbor Press, Cold Spring Harbor, N.Y. (1980)); the trp, recA, heat shock, and lacZ promoters of *E. coli* and the SV40 early promoter (Benoist, C. et al. Nature 290: 304–310 (1981)).

As far as the Shine-Dalgarno sequence is concerned, preferred examples of suitable regulatory sequences are represented by the Shine-Dalgarno of the replicase gene of the phage MS-2 and of the gene cII of bacteriophage lambda. The Shine-Dalgarno sequence may be directly followed by the DNA encoding KAT and result in the expression of the mature KAT protein.

Alternatively, the DNA encoding KAT may be preceded by a DNA sequence encoding a carrier peptide sequence. In this case, a fusion protein is produced in which the N-terminus of KAT is fused to a carrier peptide, which may help to increase the protein expression levels and intracellular stability, and provide simple means of purification. A preferred carrier peptide includes one or more of the IgG binding domains of Staphylococcus protein A. Fusion proteins comprising IgG binding domains of protein A are easily purified to homogeneity by affinity chromatography e.g. on IgG-coupled Sepharose. A DNA sequence encoding a recognition site for a proteolytic enzyme such as enterokinase, factor X or procollagenase may immediately precede the sequence for KAT to permit cleavage of the fusion protein to obtain the mature KAT protein.

Moreover, a suitable expression vector includes an appropriate marker which allows the screening of the transformed host cells. The transformation of the selected host is carried out using any one of the various techniques well known to the expert in the art and described in Maniatis et al., Molecular cloning: a laboratory manual, Second Edition, Cold Spring Harbor Press, Cold Spring Harbor, N.Y. (1989).

One further embodiment of the invention is a prokaryotic host cell transformed with the said expression vector and able to produce, under appropriate culture conditions, the KAT of the invention.

Cultures of cells derived from multicellular organisms are a desiderable host for recombinant KAT synthesis. In principal, any eukaryotic cell culture is workable, whether from vertebrate or invertebrate culture, including insect cells. Propagation of such cells in cell culture has become a routine procedure. See Tissue Culture, Academic Press, Kruse and Patterson, eds. (1973). Examples of useful host cell lines are HeLa cells, CHO and COS cell lines. The transcriptional and translational control sequences in expression vectors to be used in transforming vertebrate and invertebrate cells are often provided by viral sources. For example, commonly used promoters are derived from Adenovirus 2, polyoma and SV40. See, e. g. U.S. Pat. No. 4,599,308.

An origin of replication may be provided either by construction of the vector to include an exogenous origin or may be provided by the host cell chromosomal replication mechanism. If the vector is integrated into the host cell chromosome, the latter may be sufficient.

Rather than using vectors which contain viral origins of replication, one can transform mammalian cells by the method of cotransformation with a selectable marker and the KAT DNA. An example of a suitable marker is dihydrofolate reductase (DHFR) or thymidine kinase. See U.S. Pat. No. 4,399,216.

Cloned genes and vectors of the present invention are useful to transform cells which do not ordinarly express KAT to thereafter express this enzyme. Such cells are useful as intermediates for making recombinant KAT preparations useful for drug screening.

Moreover, genes and vectors of the present invention are useful in gene therapy. For such purposes, adenovirus vectors as well as retroviral vectors as described in U.S. Pat. No. 4,650,764 to Temin and Watanabe or U.S. Pat. No. 4,861, 719 to Miller may be employed.

Cloned genes of the present invention, and oligonucleotides derived therefrom, are useful for screening for restriction fragment length polymorphism (RFLP) associated with certain disorders.

Oligonucleotides of the present invention are useful as diagnostic tools for probing KAT gene expression in various tissues. For example, tissue can be probed in situ with oligonucleotide probes carrying detectable groups by conventional autoradiography techniques to investigate native expression of this enzyme or pathological conditions relating thereto.

Genetically modified (transfected) cells have been successfully used for cerebral implantation. Cells transfected with the KAT gene can be useful for delivering kynurenic acid (or any other KAT product; see below) to the brain. This may prove to be an attractive means to circumvent the blood-brain barrier for kynurenic acid through peripheral administration of kynurenine (or any appropriate substrate of KAT; see below).

Transfected cells expressing large quantities of KAT are also useful for the production of neuroactive kynurenic analogs. For example, KAT is capable of forming the potent NMDA receptor antagonist and neuroprotectant 7- chlorokynurenic acid from its bioprecursor L-4-chlorokynurenine (J. Med. Chem., 37, 334–336, 1994).

The present invention is explained in greater detail in the following examples. These examples are intended to be illustrative of the present invention, and should not be constructed as limiting thereof.

EXAMPLE 1

Amino Acid Sequence of Tryptic Fragments of the Rat KAT

Protein Purification

Rat KAT was prepared essentialy as described by Okuno et al. Brain Res., 534, 37–44, 1990. The enzyme eluted from a Sephacryl S-200 column was separated by HPLC on a reverse-phase column (SC18, 250×4.6 mm, Japan Spectro. Co. Ltd). Elution was performed with a gradient of solvent A (70% (vol/vol) acetonitrile in 0.1% trifluoroacetic acid (TFA)) and solvent B (0.1% TFA) applied for 40 min at a flow rate of 1 ml/min.

Trypsin and CNBr Digestion and Fragment Purification 500 pmoles of HPLC-purified rat KAT sample were digested by trypsin as described (T. E. Hughi —eds.— In: Techniques in protein chemistry, ACADEMIC PRESS, INC., p. 377–391, 1989) and by CNBr. These samples were subjected to reverse-phase HPLC after digestion and the resulting peaks collected.

Amino Acid Sequence Analysis

Sequence analysis was performed essentialy as described (Fabbrini et al. FEBS Lett., 286, 91–94, 1991). SEQ ID NO:1 shows the partial amino acid sequence of rat KAT: N-terminus of mature KAT SEQ ID NO:1, a CNBr fragment SEQ ID NO2, tryptic fragment 112 of KAT (SEQ ID NO3), and tryptic fragment 130 of KAT (SEQ ID NO:4).

EXAMPLE 2

Polymerase Chain Reaction (PCR) Cloning

RNA Extraction

Total RNA from rat kidney was extracted from small quantities of tissue according to the instruction of RNAzol™ method (RNAzol-Cinna/Biotex Lab, Tex., USA).

First Strand cDNA Synthesis

First strand cDNA was synthesized from 3 mg of total RNA using 2 mg oligo polydT (18 pb), 4 ml of dNTP (2.5 mM), 8 ml of AMV buffer (TrisHCl pH8.8 250 mM/KCl 200 mM/MgCl$_2$ 50 mM/DTT 20 mM) in a final volume of 38.75 ml. The solution was boiled for 3 minutes at 65° C. and throw in ice for 10 minutes; 0.75 ml of RNAsin (40 u/ml Promega) and 0.5 ml of AMV Reverse trascriptase (25 u/ml Boehringer Mannheim,GmbH, Germany) were added to the cold solution. The reaction was carried on at 42° C. for 2 h.

Design and Synthesis of Degenerated Oligonucleotides

Since the relative position of tryptic fragments 112 and 130, along the rat KAT primary structure, was unknown four degenerated oligonucleotides 26 bp long were designed and synthesized using a DNA/RNA synthesizer 380B Applied Biosystems. The product of the reaction was purified on Sephadex G50 (Nap 25 Column, Pharmacia).

The sense orientation oligonucleotide, OligoA: (AAYYTNTGYCARCARC AYGAYGTNGT) (SEQ ID NO:7) and the anti-sense orientation oligonucleotide, OligoC: (ACNACRTCRTGYTGYTGRCANARRTT) (SEQ ID NO:8) based on the peptide sequence Asn-Leu-Cys-Gln-Gln-His-Asp-Val-Val (residues 7–15 of fragment 130 (SEQ ID NO:4)) while the sense orientation oligonucleotide, OligoB: (ACNGANARRTTYTGRTCX ATNCCRTC) (SEQ ID NO:9) and the corresponding anti-sense oligonucleotide, OligoD: (GAYGGNATZGAYCARAAYYTNTCNGT) (SEQ ID NO:10) based on the peptide sequence Asp-Gly-Ile-Asp-Gln-Asn-Leu-Ser-Val (residues 3–11 of fragment 112) (SEQ ID NO:3) (N=T/C/A/G; Z=T/C/A; R=A/G; Y=T/C; X=T/G/A) were synthesized.

Polymerase Chain Reaction Condition

The first strand cDNA was divided in two aliquotes and amplified by PCR as described below. The two oligonucleotide, mixture PCR1: oligoA and oligoD and PCR2 oligo B and oligoC were used as primer in the PCR reaction. 70 ng of template CDNA were combined with 10 mg of each set of primers, 10 ml of 10× Taq polymerase buffer (500 mM KCl/100 mM Tris-HCl, pH 8.3), 8 ml of 25 mM MgCl$_2$, 18 ml of a dNTP solution (2.5 mM dNTP) and 0.5 ml (2.5 units) of Taq DNA polymerase (Perkin Elmer Cetus). The volume was brought to 100 ml with H$_2$O and the mixture was overlayed with mineral oil to prevent evaporation. The tube was heated to 94° C. for 3 minutes, denaturation was carried out for 3 minutes at 94° C., annealing for 2 min at 60° C. and polymerization for 2 minutes and 30 seconds at 72° C. The cycle was repeated 30 times.

A specific amplification product was observed only with PCR1. The product of the amplification was a DNA molecule of about 550 bp. The PCR1-amplification product was re-amplified using a new set of oligos, basically with the same sequence of oligoA and oligoC with SalI linkers and 5'-extra nucleotides. OligoE: (GCTAGTCGACACNACRTCRTGYTGYTGRCANARR-TT) (SEQ ID NO:11) complementary to nucleotides coding for peptide 130 (SEQ ID NO:4) and oligoF: (GATCGTCGACGAYGGNATZGAYCARAAYYTNTCN-GT) (SEQ ID NO:12) corresponding to nucleotides coding for peptide 112, (SEQ ID NO:3).

After PCR amplification the resulting DNA fragment was digested overnight with the restriction enzyme Sal1 and ligated to the Sal1 site of the cloning plasmid pUC 18 (Yanisch-Perron, C. et al.; Gene, 33:103–119, 1985). The recombinant plasmid was extracted according to the instruction of the Qiagen Plasmid Maxi Protocol; precipitated with PEG and denaturated with NaOH 2N.

Sequencing was carried out with universal and forward primer and subsequently with a series of synthetic oligonucleotide primers according to the dideoxy chain termination method (F. Sanger et al. Proc. Natl. Acad. Sci. USA 74, 5463–5467 (1977) using Sequenase (United States Biochemicals Corp., Cleveland, Ohio).

Both strands of the insert were sequenced reveealing an open reading frame of 196 amino acids. Part of the two rat KAT peptides that were sequenced are coded for the corresponding 588 bp open reading frame. This open reading frame is used as probe in the cDNA library screening described in Example 3.

EXAMPLE 3 cDNA Library Screening

About 500,000 recombinant phages of λgt11 rat kidney cDNA library (Clontec Laboratories, USA) were plated on a lawn of *E. coli* Y1090 cells. After an overnight growth at 37° C. the recombinant phages were transferred in duplicate nitrocellulose filters, their DNA was denatured, neutralized and baked under vacuum at 80° C. for 2 h. Prehybridization was carried out at 60° C. for 4 h in 6xSSC (1X SSC: ), 5x Denhardt's (1X Denhardt: ), 1% SDS, 200 ug/ml salmon sperm DNA. The filters were then hybridized overnight at 60° C. in the same mixture with the addition of about 1.5×10$^6$ cpm/ml of labeled probe (see Example 2). The probe was labeled with ($^{32}$p) dCTP by Multiprime DNA labelling system (Amersham), purified on Nick Column (Pharmacia) and added to the hybridizing solution. The filters were washed at 60° C. twice in 2xSSC, 0.1% SDS and ones in 1xSSC, 1%SDS. Filters were exposed to Kodak X-AR film (Eastman Kodak Company, Rochester, N.Y., USA) with intensifying screen at −80° C.

Positive phage plaques were isolated and screened again twice in order to isolate single clones.

Recombinant Phage DNA Extraction and Sequencing Methods

About 50,000 phages of each positive clone were plated on a lawn of *E. coli* Y1090 cells. After an overnight growth at 37° C. phages were resuspended in SM buffer (100 mM NaCl/8 mM MgSO$_4$/50 mM Tris-HCl, pH 7.5 /gelatin 0.001%) and chloroform 0.3%; the suspension was treated with 1 mg of RNAse and 1 mg of DNAse. Phage DNA was precipitated with PEG 10%/1M NaCl, extracted with phenol and phenol:chloroform:iso-amyl alcohol and precipitated with PEG again.

The phage DNA was digested with EcoRI and the insert was ligated to the EcoRI site of pUC18.

The recombinant plasmid was extracted according to the instruction of Qiagen Plasmid Maxi Protocol; precipitated with PEG and denaturated with 2N NaOH .

Sequencing was carried out with universal and forward primer and subsequently with a series of synthetic oligonucleotide primers according to the dideoxy chain termination method (F. Sanger et al. Proc. Natl. Acad. Sci. USA 74, 5463–5467 (1977)) using Sequenase (United States Biochemicals Corp., Cleveland, Ohio).

Two positive clones were isolated, cDNA-1 and CDNA-2. Both strands of the two CDNAs were sequenced. (see SEQ ID NO:5 and 6).

CDNA-1 encodes a deduced protein of 423 amino acid residues whereas cDNA-2 encodes a deduced protein of 437 amino acid residues.

The two deduced proteins differ only in their N-terminus Moreover, the cDNA-2 clone is not homogeneous, since an alternative 5' sequence introduces an upstream ATG starting codon. The two alternative protein sequences predicted by the cDNA-2 clone are both illustrated in SEQ ID NO:6.

As already said, the 437 amino acids long protein deduced from the cDNA-2 clone presents a putative mitochondrial transit peptide in position 1 to 24 which is only partially present in the 423 amino acid long protein.

EXAMPLE 4

Expression in Mammalian Cells

The expression plasmid encoding rat KAT was constructed as follows. a) To remove the 5' and the 3' untranslated sequences, as well as the putative mitochondrial targeting peptide, PCR amplification was performed using two specific oligonucleotides with XhoI linkers. The sense orientation oligonucleotide (5'-TGTCCTCGAGACCATGACCAAACGGCTGCAGGCTCGGA-3') (SEQ ID NO:13) begins at +241 of cDNA-1, whereas the antisense-orientation oligonucleotide(5'-GTACCTCGAGTCAGGGTTGGAGCTCTTTCCACTTG-3') (SEQ ID NO:14) complements the sequence starting from the end of the coding sequence. The XhoI-digested fragment, after being controlled by sequencing, was cloned into the XhoI site of pSVL expression vector (Pharmacia Biotechnology). COS-1 cells were transfected with 10 ug of PSVL-KAT plasmid by calcium phosphate method (Maniatis et al., Molecular cloning: a laboratory manual, Second Edition, Cold Spring Harbor Press, Cold Spring Harbor, N.Y. (1989)). 72 hours after transfection, cells were disrupted by freezing and thawing and after centrifugation the supernatant was used for KAT and glutamine transaminase K activities.

EXAMPLE 5

Kynurenine Amino Transferase and Glutamine Amino Transferase K Activities

Kynurenine Transaminase Assay

The reaction mixture (100 ul) contained 70 uM pyridoxal phosphate, 5 mM pyruvate, 3 mM kynurenine, and KAT sample in 0.17 M potassium phosphate buffer, pH 8.1, and was incubated at 37° C. for 30 min and 1 h. Reaction was stopped by adding 20 ul TCA 50% and the precipitate was removed by centrifugation. The supernatant was analyzed by HPLC with a C18 column (Vydac 201TP54, 25×4.6 cmxmm) at 1 ml/min, equilibrated with 5 mM acetic acid, 5% methanol, 0.1% heptane sulfonic acid, pH 3.0, and kynurenic acid was eluted with 50 mM acetic acid, 5% methanol, 0.5% heptane sulfonic acid, pH 4.5. Absorbance at 243 nm was measured.

Glutamine Transaminase K Assay

Glutamine transaminase K activity was measured as described by Cooper and Meister (Methods Enzymol., 113, 344–349, 1985).

We claim:

1. An isolated and purified rat KAT enzyme which is coded for by an isolated DNA sequence comprising the sequence of cDNA-1 (SEQ ID NO:5) or cDNA-2 (SEQ ID NO:6).

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Leu  Gln  Ala  Xaa  Xaa  Leu  Asp  Gly  Ile  Asp  Gln  Asn
 1                  5                        10

Leu  Xaa  Val  Glu  Phe  Gly  Lys  Thr  Xaa  Glu  Tyr
         15                       20
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear     ( i i ) MOLECULE TYPE: peptide ( x i ) SEQUENCE DESCRIPTION: SEQ ID NO:2:

Xaa Xaa Leu Pro Gly Ala Glu Asp Gly Pro Tyr
 1               5                           10

Asp Arg Arg Xaa Ala
             15

( 2 ) INFORMATION FOR SEQ ID NO:3:

( i ) SEQUENCE CHARACTERISTICS:
           ( A ) LENGTH: 14 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:3:

Arg Leu Asp Gly Ile Asp Gln Asn Leu
 1               5

Ser Val Glu Phe Gly
 10

( 2 ) INFORMATION FOR SEQ ID NO:4:

( i ) SEQUENCE CHARACTERISTICS:
           ( A ) LENGTH: 31 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:4:

Xaa Glu Leu Glu Leu Val Ala Asn Leu Cys Gln Gln
 1               5                           10

His Asp Val Cys Ile Ser Asp Glu Val Tyr Gln Gln
             15                  20

Val Tyr Asp Leu Gly His Gln
 25                  30

( 2 ) INFORMATION FOR SEQ ID NO:5:

( i ) SEQUENCE CHARACTERISTICS:
           ( A ) LENGTH: 1893 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:5:

| | | | | | |
|---|---|---|---|---|---|
| AAACTGACCA | AGGAGTATGA | TCAATCCCGT | CCAGCCTCCG | AGCCTGCAGC | 50 |
| CGTTTGGTCA | TGGTGAGCTG | CTTCAGCTAA | CAATTGCACT | GACAGTGCTC | 100 |
| TTGAGCCAAG | TTGCTTCTGG | GCGGAAGTAG | TCCATCTAGG | GCTCGGCCTC | 150 |
| TTTAAAGAAA | CAGACTTCTG | CAACCTTGGG | ACTACGTTTG | GGGTCGCCGG | 200 |
| CTATTGGACG | GAGCAGCGCA | ATTGTTAGCT | GAAGCAGCTC | ACC ATG ACC | 249 |
|            |            |            |            | Met Thr    |     |
|            |            |            |            |  1         |     |

AAA CGG CTG CAG GCT CGG AGG CTG GAC GGG ATT GAT CAA AAC                291
Lys Arg Leu Gln Ala Arg Arg Leu Asp Gly Ile Asp Gln Asn
        5                   10                  15

CTC TGG GTG GAG TTT GGC AAA CTG ACC AAG GAG TAT GAC GTC                333

-continued

| | | | | | | | | | | | | |
|---|---|---|---|---|---|---|---|---|---|---|---|---|
| Leu | Trp | Val | Glu<br>20 | Phe | Gly | Lys | Leu | Thr<br>25 | Lys | Glu | Tyr | Asp Val<br>30 |

| GTG | AAC | TTG | GGT | CAG | GGC | TTC | CCT | GAC | TTC | TCG | CCT | CCG | GAC | 375 |
|---|---|---|---|---|---|---|---|---|---|---|---|---|---|---|
| Val | Asn | Leu | Gly<br>35 | Gln | Gly | Phe | Pro | Asp<br>40 | Phe | Ser | Pro | Pro | Asp | |

| TTT | GCA | ACG | CAA | GCT | TTT | CAG | CAG | GCT | ACC | AGT | GGG | AAC | TTC | 417 |
|---|---|---|---|---|---|---|---|---|---|---|---|---|---|---|
| Phe<br>45 | Ala | Thr | Gln | Ala | Phe<br>50 | Gln | Gln | Ala | Thr | Ser<br>55 | Gly | Asn | Phe | |

| ATG | CTC | AAC | CAG | TAC | ACC | AGG | GCA | TTT | GGT | TAC | CCA | CCA | CTG | 459 |
|---|---|---|---|---|---|---|---|---|---|---|---|---|---|---|
| Met | Leu<br>60 | Asn | Gln | Tyr | Thr | Arg<br>65 | Ala | Phe | Gly | Tyr | Pro<br>70 | Pro | Leu | |

| ACA | AAC | GTC | CTG | GCA | AGT | TTC | TTT | GGC | AAG | CTG | CTG | GGA | CAG | 501 |
|---|---|---|---|---|---|---|---|---|---|---|---|---|---|---|
| Thr | Asn | Val<br>75 | Leu | Ala | Ser | Phe | Phe<br>80 | Gly | Lys | Leu | Leu | Gly<br>85 | Gln | |

| GAG | ATG | GAC | CCA | CTC | ACG | AAT | GTG | CTG | GTG | ACA | GTG | GGT | GCC | 543 |
|---|---|---|---|---|---|---|---|---|---|---|---|---|---|---|
| Glu | Met | Asp | Pro<br>90 | Leu | Thr | Asn | Val | Leu<br>95 | Val | Thr | Val | Gly | Ala<br>100 | |

| TAT | GGG | GCC | TTG | TTC | ACA | GCC | TTT | CAG | GCC | CTG | GTG | GAT | GAA | 585 |
|---|---|---|---|---|---|---|---|---|---|---|---|---|---|---|
| Tyr | Gly | Ala | Leu | Phe<br>105 | Thr | Ala | Phe | Gln | Ala<br>110 | Leu | Val | Asp | Glu | |

| GGA | GAT | GAG | GTC | ATC | ATC | ATG | GAA | CCT | GCT | TTT | GAC | TGT | TAT | 627 |
|---|---|---|---|---|---|---|---|---|---|---|---|---|---|---|
| Gly<br>115 | Asp | Glu | Val | Ile | Ile<br>120 | Met | Glu | Pro | Ala | Phe<br>125 | Asp | Cys | Tyr | |

| GAA | CCC | ATG | ACA | ATG | ATG | GCT | GGA | GGT | TGC | CCT | GTG | TTC | GTG | 669 |
|---|---|---|---|---|---|---|---|---|---|---|---|---|---|---|
| Glu | Pro<br>130 | Met | Thr | Met | Met<br>135 | Ala | Gly | Gly | Cys | Pro<br>140 | Val | Phe | Val | |

| ACT | CTG | AAG | CCG | AGC | CCT | GCT | CCT | AAG | GGG | AAA | CTG | GGA | GCC | 711 |
|---|---|---|---|---|---|---|---|---|---|---|---|---|---|---|
| Thr | Leu | Lys<br>145 | Pro | Ser | Pro | Ala | Pro<br>150 | Lys | Gly | Lys | Leu | Gly<br>155 | Ala | |

| AGC | AAT | GAT | TGG | CAA | CTG | GAT | CCT | GCA | GAA | CTG | GCC | AGC | AAG | 753 |
|---|---|---|---|---|---|---|---|---|---|---|---|---|---|---|
| Ser | Asn | Asp | Trp<br>160 | Gln | Leu | Asp | Pro | Ala<br>165 | Glu | Leu | Ala | Ser | Lys<br>170 | |

| TTC | ACA | CCT | CGC | ACC | AAG | GTC | CTG | GTC | CTC | AAC | ACA | CCC | AAC | 795 |
|---|---|---|---|---|---|---|---|---|---|---|---|---|---|---|
| Phe | Thr | Pro | Arg | Thr<br>175 | Lys | Val | Leu | Val | Leu<br>180 | Asn | Thr | Pro | Asn | |

| AAC | CCT | TTA | GGA | AAG | GTA | TTC | TCT | AGG | ATG | GAG | CTG | GAG | CTG | 837 |
|---|---|---|---|---|---|---|---|---|---|---|---|---|---|---|
| Asn<br>185 | Pro | Leu | Gly | Lys | Val<br>190 | Phe | Ser | Arg | Met | Glu<br>195 | Leu | Glu | Leu | |

| GTG | GCT | AAT | CTG | TGC | CAG | CAG | CAC | GAT | GTC | GTG | TGC | ATC | TCT | 879 |
|---|---|---|---|---|---|---|---|---|---|---|---|---|---|---|
| Val | Ala | Asn<br>200 | Leu | Cys | Gln | Gln | His<br>205 | Asp | Val | Val | Cys | Ile<br>210 | Ser | |

| GAT | GAG | GTC | TAC | CAG | TGG | CTG | GTC | TAT | GAC | GGG | CAC | CAG | CAC | 921 |
|---|---|---|---|---|---|---|---|---|---|---|---|---|---|---|
| Asp | Glu | Val | Tyr<br>215 | Gln | Trp | Leu | Val | Tyr<br>220 | Asp | Gly | His | Gln | His<br>225 | |

| GTC | AGC | ATC | GCC | AGC | CTC | CCT | GGC | ATG | TGG | GAT | CGG | ACC | CTG | 963 |
|---|---|---|---|---|---|---|---|---|---|---|---|---|---|---|
| Val | Ser | Ile | Ala | Ser<br>230 | Leu | Pro | Gly | Met | Trp<br>235 | Asp | Arg | Thr | Leu<br>240 | |

| ACC | ATC | GGC | AGT | GCA | GGC | AAA | AGC | TTC | AGT | GCC | ACT | GGC | TGG | 1005 |
|---|---|---|---|---|---|---|---|---|---|---|---|---|---|---|
| Thr | Ile | Gly | Ser | Ala<br>245 | Gly | Lys | Ser | Phe | Ser<br>250 | Ala | Thr | Gly | Trp | |

| AAG | GTG | GGC | TGG | GTC | ATG | GGT | CCA | GAT | AAC | ATC | ATG | AAG | CAC | 1047 |
|---|---|---|---|---|---|---|---|---|---|---|---|---|---|---|
| Lys | Val<br>255 | Gly | Trp | Val | Met<br>260 | Gly | Pro | Asp | Asn | Ile<br>265 | Met | Lys | His | |

| CTG | AGG | ACA | GTG | CAC | CAG | AAT | TCT | ATC | TTC | CAC | TGC | CCC | ACC | 1089 |
|---|---|---|---|---|---|---|---|---|---|---|---|---|---|---|
| Leu | Arg | Thr<br>270 | Val | His | Gln | Asn | Ser<br>275 | Ile | Phe | His | Cys | Pro<br>280 | Thr | |

| CAG | GCC | CAG | GCT | GCA | GTA | GCC | CAG | TGC | TTT | GAG | CGG | GAG | CAG | 1131 |
|---|---|---|---|---|---|---|---|---|---|---|---|---|---|---|
| Gln | Ala | Gln | Ala<br>285 | Ala | Val | Ala | Gln | Cys<br>290 | Phe | Glu | Arg | Glu | Gln<br>295 | |

| CAA | CAC | TTT | GGA | CAA | CCC | AGC | AGC | TAC | TTT | TTG | CAG | CTG | CCA | 1173 |
|---|---|---|---|---|---|---|---|---|---|---|---|---|---|---|

|  |  |  |  |  |  |  |  |  |  |  |
|---|---|---|---|---|---|---|---|---|---|---|
| Gln | His | Phe | Gly<br>300 | Gln | Pro | Ser | Ser<br>305 | Tyr | Phe | Leu | Gln | Leu | Pro<br>310 |

| CAG | GCC | ATG | GAG | CTG | AAC | CGA | GAC | CAC | ATG | ATC | CGT | AGC | CTG | 1215 |
| Gln | Ala | Met | Glu | Leu<br>315 | Asn | Arg | Asp | His | Met<br>320 | Ile | Arg | Ser | Leu |

| CAG | TCA | GTG | GGC | CTC | AAG | CTC | TGG | ATC | TCC | CAG | GGG | AGC | TAC | 1257 |
| Gln<br>325 | Ser | Val | Gly | Leu | Lys<br>330 | Leu | Trp | Ile | Ser | Gln<br>335 | Gly | Ser | Tyr |

| TTC | CTC | ATT | GCA | GAC | ATC | TCA | GAC | TTC | AAG | AGC | AAG | ATG | CCT | 1299 |
| Phe | Leu | Ile<br>340 | Ala | Asp | Ile | Ser | Asp<br>345 | Phe | Lys | Ser | Lys | Met<br>350 | Pro |

| GAC | CTG | CCC | GGA | GCT | GAG | GAT | GAG | CCT | TAT | GAC | AGA | CGC | TTT | 1341 |
| Asp | Leu | Pro<br>355 | Gly | Ala | Glu | Asp | Glu<br>360 | Pro | Tyr | Asp | Arg | Arg<br>365 | Phe |

| GCC | AAG | TGG | ATG | ATC | AAA | AAC | ATG | GGC | TTG | GTG | GGC | ATC | CCT | 1383 |
| Ala | Lys | Trp | Met<br>370 | Ile | Lys | Asn | Met | Gly<br>375 | Leu | Val | Gly | Ile | Pro<br>380 |

| GTC | TCC | ACA | TTC | TTC | AGT | CGG | CCC | CAT | CAG | AAG | GAC | TTT | GAC | 1425 |
| Val | Ser | Thr | Phe | Phe<br>385 | Ser | Arg | Pro | His | Gln<br>390 | Lys | Asp | Phe | Asp |

| CAC | TAC | ATC | CGA | TTC | TGT | TTT | GTC | AAG | GAC | AAG | GCC | ACA | CTC | 1467 |
| His<br>395 | Tyr | Ile | Arg | Phe | Cys<br>400 | Phe | Val | Lys | Asp | Lys<br>405 | Ala | Thr | Leu |

| CAG | GCC | ATG | GAT | GAG | AGA | CTG | CGC | AAG | TGG | AAA | GAG | CTC | CAA | 1509 |
| Gln | Ala | Met | Asp<br>410 | Glu | Arg | Leu | Arg<br>415 | Lys | Trp | Lys | Glu<br>420 | Leu | Gln |

| CCC | TGAGGAGGCT | GCCCTCAGCC | CCACCTCGAA | CACAGGCCTC | AGCTATGCCT | 1562 |
| Pro |

| TAGCACAGGG | ATGGCACTGG | AGGGCCCAGC | TGTGTGACTG | CGCATGTTTC | 1612 |
| CAGAAAAGAG | GCCATGTCTT | GGGGGTTGAA | GCCATCCTTT | CCCAGTGTCC | 1662 |
| ATCTGGACTA | TTGGGTTGGG | GGCCAGTTCT | GGGTCTCAGC | CTACTCCTCT | 1712 |
| GTAGGTTGCC | TGTAGGGTTT | TGATTGTTTC | TGGCCTCTCT | GCCTGGGGCA | 1762 |
| GGAAAGGGTG | GAATATCAGG | CCCGGTACCA | CCTTAGCCCT | GCCGAGGCTC | 1812 |
| TGTGGCTTCT | CTACATCTTC | TCCTGTGACC | TCAGGATGTT | GCTACTGTTC | 1862 |
| CTAATAAAGT | TTAAGTTAT | TAGGACCCTC | A | | 1893 |

( 2 ) INFORMATION FOR SEQ ID NO:6:

( i ) SEQUENCE CHARACTERISTICS:
        ( A ) LENGTH: 2304 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:6:

| GGGCGACTCT | AGATTTTTTT | TTTTTTTTAC | CTTCTACCTT | TTATTGTCAC | 50 |
| GTGAACCATG | GTCCTACAGG | CTGCTGACAA | GCTTGGCTGA | GCAGGGATCC | 100 |
| CAGGGGCGTC | GGCAGGAGAT | GAGGAAGGGT | TGCTGGGAGG | GCTTGGCCTC | 150 |
| TTCCTTGAGA | AGACAGCAAA | TGTATCCAGC | CTAGATTAAG | GGTAGGGCAT | 200 |
| CCCCTATCCC | TGTCAGTGGG | CCTAGATCTC | AGAGCCCAC | ATTAAAGACT | 250 |
| GCTAATGGGT | CAGAAATGGG | GGTCCCTTAG | ATGGGGTAG | GCAGCAAGGC | 300 |
| CCTCCCTCCA | GTGTTCTCAT | TCTGTTCCGG | TTTCATTTGT | TGTGTCCAGG | 350 |
| GACGGTGAAG | CAGATACCAG | TCTCAAGCCC | CAGGGTGCAG | GAAGACGGGA | 400 |

```
AATGGGAAAA TGGAAACATT CTTCAAGTGA CCAGAGCACT CTGCCGGGGA                                              450

CAAAAGACTT TGCCTTGAAC GCGTAGTGGA GAAGCTACAA ACCCCAGGTC                                              500

CCAGTGGCCT GATTGACTTA GGGTCTCAGC TGGCCCAAAA CTCAGTGTGT                                              550

AGATCAGACT GATCTCAAAC TCACAGAGAT CTCCCTGCCT TTGCCTGCTG                                              600

AGTCCTGGGA TTAAAGGC ATG AAT CAC AGT ACC TGG TGC CTT TTC                                             645
                     Met Asn His Ser Thr Trp Cys Leu Phe
                      1                   5

TTT AAA AAG CTC ACC ATG ACC AAA CGG CTG CAG GCT CGG AGG                                             687
Phe Lys Lys Leu Thr Met Thr Lys Arg Leu Gln Ala Arg Arg
 10              15                      20

Met Thr Lys Arg Leu Gln Ala Arg Arg
                     1                       10

CTG GAC GGG ATT GAT CAA AAC CTC TGG GTG GAG TTT GGC AAA                                             729
Leu Asp Gly Ile Asp Gln Asn Leu Trp Val Glu Phe Gly Lys
 25              30                      40

Leu Asp Gly Ile Asp Gln Asn Leu Trp Val Glu Phe Gly Lys
 15              20                      25

CTG ACC AAG GAG TAT GAC GTC GTG AAC TTG GGT CAG GGC TTC                                             771
Leu Thr Lys Glu Tyr Asp Val Val Asn Leu Gly Gln Gly Phe
     45                  50                      55

Leu Thr Lys Glu Tyr Asp Val Val Asn Leu Gly Gln Gly Phe
     30                  35                      40

CCT GAC TTC TCG CCT CCG GAC TTT GCA ACG CAA GCT TTT CAG                                             813
Pro Asp Phe Ser Pro Pro Asp Phe Ala Thr Gln Ala Phe Gln
             60                  65                  70

Pro Asp Phe Ser Pro Pro Asp Phe Ala Thr Gln Ala Phe Gln
             45                  50                  55

CAG GCT ACC AGT GGG AAC TTC ATG CTC AAC CAG TAC ACC AGG                                             855
Gln Ala Thr Ser Gly Asn Phe Met Leu Asn Gln Tyr Thr Arg
                 75                  80

Gln Ala Thr Ser Gly Asn Phe Met Leu Asn Gln Tyr Thr Arg
                 60                  65

GCA TTT GGT TAC CCA CCA CTG ACA AAC GTC CTG GCA AGT TTC                                             897
Ala Phe Gly Tyr Pro Pro Leu Thr Asn Val Leu Ala Ser Phe
 80                  90                      95

Ala Phe Gly Tyr Pro Pro Leu Thr Asn Val Leu Ala Ser Phe
 70                  75                      80

TTT GGC AAG CTG CTG GGA CAG GAG ATG GAC CCA CTC ACG AAT                                             939
Phe Gly Lys Leu Leu Gly Gln Glu Met Asp Pro Leu Thr Asn
     100                 105                     110

Phe Gly Lys Leu Leu Gly Gln Glu Met Asp Pro Leu Thr Asn
     85                  90                      95

GTG CTG GTG ACA GTG GGT GCC TAT GGG GCC TTG TTC ACA GCC                                             981
Val Leu Val Thr Val Gly Ala Tyr Gly Ala Leu Phe Thr Ala
         115                 120                 125

Val Leu Val Thr Val Gly Ala Tyr Gly Ala Leu Phe Thr Ala
         100                 105                 110

TTT CAG GCC CTG GTG GAT GAA GGA GAT GAG GTC ATC ATC ATG                                             1023
Phe Gln Ala Leu Val Asp Glu Gly Asp Glu Val Ile Ile Met
             130                 135                 140

Phe Gln Ala Leu Val Asp Glu Gly Asp Glu Val Ile Ile Met
             115                 120                 125

GAA CCT GCT TTT GAC TGT TAT GAA CCC ATG ACA ATG ATG GCT                                             1065
Glu Pro Ala Phe Asp Cys Tyr Glu Pro Met Thr Met Met Ala
                 145                 150
```

```
Glu  Pro  Ala  Phe  Asp  Cys  Tyr  Glu  Pro  Met  Thr  Met  Met  Ala
               130                      135

GGA  GGT  TGC  CCT  GTG  TTC  GTG  ACT  CTG  AAG  CCG  AGC  CCT  GCT        1107
Gly  Gly  Cys  Pro  Val  Phe  Val  Thr  Leu  Lys  Pro  Ser  Pro  Ala
155                 160                      165

Gly  Gly  Cys  Pro  Val  Phe  Val  Thr  Leu  Lys  Pro  Ser  Pro  Ala
140                 145                                     150

CCT  AAG  GGG  AAA  CTG  GGA  GCC  AGC  AAT  GAT  TGG  CAA  CTG  GAT        1149
Pro  Lys  Gly  Lys  Leu  Gly  Ala  Ser  Asn  Asp  Trp  Gln  Leu  Asp
     170                      175                      180

Pro  Lys  Gly  Lys  Leu  Gly  Ala  Ser  Asn  Asp  Trp  Gln  Leu  Asp
     155                      160                      165

CCT  GCA  GAA  CTG  GCC  AGC  AAG  TTC  ACA  CCT  CGC  ACC  AAG  GTC        1191
Pro  Ala  Glu  Leu  Ala  Ser  Lys  Phe  Thr  Pro  Arg  Thr  Lys  Val
          185                      190                      195

Pro  Ala  Glu  Leu  Ala  Ser  Lys  Phe  Thr  Pro  Arg  Thr  Lys  Val
          170                      175                      180

CTG  GTC  CTC  AAC  ACA  CCC  AAC  AAC  CCT  TTA  GGA  AAG  GTA  TTC        1233
Leu  Val  Leu  Asn  Thr  Pro  Asn  Asn  Pro  Leu  Gly  Lys  Val  Phe
               200                      205                      210

Leu  Val  Leu  Asn  Thr  Pro  Asn  Asn  Pro  Leu  Gly  Lys  Val  Phe
               185                      190                      195

TCT  AGG  ATG  GAG  CTG  GAG  CTG  GTG  GCT  AAT  CTG  TGC  CAG  CAG        1275
Ser  Arg  Met  Glu  Leu  Glu  Leu  Val  Ala  Asn  Leu  Cys  Gln  Gln
                    215                      220

Ser  Arg  Met  Glu  Leu  Glu  Leu  Val  Ala  Asn  Leu  Cys  Gln  Gln
                    200                      205

CAC  GAT  GTC  GTG  TGC  ATC  TCT  GAT  GAG  GTC  TAC  CAG  TGG  CTG        1317
His  Asp  Val  Val  Cys  Ile  Ser  Asp  Glu  Val  Tyr  Gln  Trp  Leu
225                      230                      235

His  Asp  Val  Val  Cys  Ile  Ser  Asp  Glu  Val  Tyr  Gln  Trp  Leu
210                      215                      220

GTC  TAT  GAC  GGG  CAC  CAG  CAC  GTC  AGC  ATC  GCC  AGC  CTC  CCT        1359
Val  Try  Asp  Gly  His  Gln  His  Val  Ser  Ile  Ala  Ser  Leu  Pro
     240                      245                      250

Val  Try  Asp  Gly  His  Gln  His  Val  Ser  Ile  Ala  Ser  Leu  Pro
     225                      230                      235

GGC  ATG  TGG  GAT  CGG  ACC  CTG  ACC  ATC  GGC  AGT  GCA  GGC  AAA        1401
Gly  Met  Trp  Asp  Arg  Thr  Leu  Thr  Ile  Gly  Ser  Ala  Gly  Lys
          255                      260                      265

Gly  Met  Trp  Asp  Arg  Thr  Leu  Thr  Ile  Gly  Ser  Ala  Gly  Lys
          240                      245                      250

AGC  TTC  AGT  GCC  ACT  GGC  TGG  AAG  GTG  GGC  TGG  GTC  ATG  GGT        1443
Ser  Phe  Ser  Ala  Thr  Gly  Trp  Lys  Val  Gly  Trp  Val  Met  Gly
               270                      275                      280

Ser  Phe  Ser  Ala  Thr  Gly  Trp  Lys  Val  Gly  Trp  Val  Met  Gly
               255                      260                      265

CCA  GAT  AAC  ATC  ATG  AAG  CAC  CTG  AGG  ACA  GTG  CAC  CAG  AAT        1485
Pro  Asp  Asn  Ile  Met  Lys  His  Leu  Arg  Thr  Val  His  Gln  Asn
                    285                      290

Pro  Asp  Asn  Ile  Met  Lys  His  Leu  Arg  Thr  Val  His  Gln  Asn
                    270                      275

TCT  ATC  TTC  CAC  TGC  CCC  ACC  CAG  GCC  CAG  GCT  GCA  GTA  GCC        1527
Ser  Ile  Phe  His  Cys  Pro  Thr  Gln  Ala  Gln  Ala  Ala  Val  Ala
295                      300                      305

Ser  Ile  Phe  His  Cys  Pro  Thr  Gln  Ala  Gln  Ala  Ala  Val  Ala
280                      285                      290
```

| | | | | | | | | | | | | | | |
|---|---|---|---|---|---|---|---|---|---|---|---|---|---|---|
| CAG | TGC | TTT | GAG | CGG | GAG | CAG | CAA | CAC | TTT | GGA | CAA | CCC | AGC | 1569 |
| Gln | Cys | Phe | Glu | Arg | Glu | Gln | Gln | His | Phe | Gly | Gln | Pro | Ser | |
| | 310 | | | | 315 | | | | | 320 | | | | |

Gln Cys Phe Glu Arg Glu Gln Gln His Phe Gly Gln Pro Ser
295 300 305

| | | | | | | | | | | | | | | |
|---|---|---|---|---|---|---|---|---|---|---|---|---|---|---|
| AGC | TAC | TTT | TTG | CAG | CTG | CCA | CAG | GCC | ATG | GAG | CTG | AAC | CGA | 1611 |
| Ser | Tyr | Phe | Leu | Gln | Leu | Pro | Gln | Ala | Met | Glu | Leu | Asn | Arg | |
| | | 325 | | | | 330 | | | | | 335 | | | |

Ser Tyr Phe Leu Gln Leu Pro Gln Ala Met Glu Leu Asn Arg
310 315 320

| | | | | | | | | | | | | | | |
|---|---|---|---|---|---|---|---|---|---|---|---|---|---|---|
| GAC | CAC | ATG | ATC | CGT | AGC | CTG | CAG | TCA | GTG | GGC | CTC | AAG | CTC | 1653 |
| Asp | His | Met | Ile | Arg | Ser | Leu | Gln | Ser | Val | Gly | Leu | Lys | Leu | |
| | | | 340 | | | | | 345 | | | | | 350 | |

Asp His Met Ile Arg Ser Leu Gln Ser Val Gly Leu Lys Leu
325 330 335

| | | | | | | | | | | | | | | |
|---|---|---|---|---|---|---|---|---|---|---|---|---|---|---|
| TGG | ATC | TCC | CAG | GGG | AGC | TAC | TTC | CTC | ATT | GCA | GAC | ATC | TCA | 1695 |
| Trp | Ile | Ser | Gln | Gly | Ser | Tyr | Phe | Leu | Ile | Ala | Asp | Ile | Ser | |
| | | | | 355 | | | | | 360 | | | | | |

Trp Ile Ser Gln Gly Ser Tyr Phe Leu Ile Ala Asp Ile Ser
340 345

| | | | | | | | | | | | | | | |
|---|---|---|---|---|---|---|---|---|---|---|---|---|---|---|
| GAC | TTC | AAG | AGC | AAG | ATG | CCT | GAC | CTG | CCC | GGA | GCT | GAG | GAT | 1737 |
| Asp | Phe | Lys | Ser | Lys | Met | Pro | Asp | Leu | Pro | Gly | Ala | Glu | Asp | |
| 365 | | | | | 370 | | | | | 375 | | | | |

Asp Phe Lys Ser Lys Met Pro Asp Leu Pro Gly Ala Glu Asp
350 355 360

| | | | | | | | | | | | | | | |
|---|---|---|---|---|---|---|---|---|---|---|---|---|---|---|
| GAG | CCT | TAT | GAC | AGA | CGC | TTT | GCC | AAG | TGG | ATG | ATC | AAA | AAC | 1779 |
| Glu | Pro | Tyr | Asp | Arg | Arg | Phe | Ala | Lys | Trp | Met | Ile | Lys | Asn | |
| | 380 | | | | | 385 | | | | | 390 | | | |

Glu Pro Tyr Asp Arg Arg Phe Ala Lys Trp Met Ile Lys Asn
365 370 375

| | | | | | | | | | | | | | | |
|---|---|---|---|---|---|---|---|---|---|---|---|---|---|---|
| ATG | GGC | TTG | GTG | GGC | ATC | CCT | GTC | TCC | ACA | TTC | TTC | AGT | CGG | 1821 |
| Met | Gly | Leu | Val | Gly | Ile | Pro | Val | Ser | Thr | Phe | Phe | Ser | Arg | |
| | | | 395 | | | | | 400 | | | | | 405 | |

Met Gly Leu Val Gly Ile Pro Val Ser Thr Phe Phe Ser Arg
380 385 390

| | | | | | | | | | | | | | | |
|---|---|---|---|---|---|---|---|---|---|---|---|---|---|---|
| CCC | CAT | CAG | AAG | GAC | TTT | GAC | CAC | TAC | ATC | CGA | TTC | TGT | TTT | 1863 |
| Pro | His | Gln | Lys | Asp | Phe | Asp | His | Tyr | Ile | Arg | Phe | Cys | Phe | |
| | | | 410 | | | | | 415 | | | | | 420 | |

Pro His Gln Lys Asp Phe Asp His Tyr Ile Arg Phe Cys Phe
395 400 405

| | | | | | | | | | | | | | | |
|---|---|---|---|---|---|---|---|---|---|---|---|---|---|---|
| GTC | AAG | GAC | AAG | GCC | ACA | CTC | CAG | GCC | ATG | GAT | GAG | AGA | CTG | 1905 |
| Val | Lys | Asp | Lys | Ala | Thr | Leu | Gln | Ala | Met | Asp | Glu | Arg | Leu | |
| | | | | 425 | | | | | 430 | | | | | |

Val Lys Asp Lys Ala Thr Leu Gln Ala Met Asp Glu Arg Leu
410 415

| | | | | | | | |
|---|---|---|---|---|---|---|---|
| CGC | AAG | TGG | AAA | GAG | CTC | CAA | CCC TGAGGAGGCT GCCCTCAGCC | 1949 |
| Arg | Lys | Trp | Lys | Glu | Leu | Gln | Pro | |
| 435 | | | | | 440 | | | |

Arg Lys Trp Lys Glu Leu Gln Pro
420 425

| | | | |
|---|---|---|---|
| CCACCTCGAA CACAGGCCTC AGCTATGCCT TAGCACAGGG ATGGCACTGG | 1999 |
| AGGGCCCAGC TGTGTGACTG CGCATGTTTC CAGAAAAGAG GCCATGTCTT | 2049 |
| GGGGGTTGAA GCCATCCTTT CCCAGTGTCC ATCTGGACTA TTGGGTTGGG | 2099 |
| GGCCAGTTCT GGGTCTCAGC CTACTCCTCT GTAGGTTGCC TGTAGGGTTT | 2149 |
| TGATTGTTTC TGGCCTCTCT GCCTGGGGCA GGAAAGGGTG GAATATCAGG | 2199 |

| | |
|---|---|
| CCCGGTACCA CCTTAGCCCT GCCGAGGCTC TGTGGCTTCT CTACATCTTC | 2249 |
| TCCTGTGACC TCAGGATGTT GCTACTGTTC CTAATAAAGT TTTAAGTTAT | 2299 |
| TAGGA | 2304 |

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:7:

| | |
|---|---|
| AAYYTNTGYC ARCARCAYGA YGTNGT | 26 |

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:8:

| | |
|---|---|
| ACNACRTCRT GYTGYTGRCA NARRTT | 26 |

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:9:

| | |
|---|---|
| ACNGANARRT TYTGRTCDAT NCCRTC | 26 |

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:10:

| | |
|---|---|
| GAYGGNATHG AYCARAAYYT NTCNGT | 26 |

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:11:

| | |
|---|---|
| GCTAGTCGAC ACNACRTCRT GYTGYTGRCA NARRTT | 36 |

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:12:

GATCGTCGAC GAYGGNATHG AYCARAAYYT NTCNGT    36

( 2 ) INFORMATION FOR SEQ ID NO:13:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:13:

TGTCCTCGAG ACCATGACCA AACGGCTGCA GGCTCGGA    38

( 2 ) INFORMATION FOR SEQ ID NO:14:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:14:

GTACCTCGAG TCAGGGTTGG AGCTCTTTCC ACTTG    35